(12) United States Patent
Hemker et al.

(10) Patent No.: US 6,740,496 B1
(45) Date of Patent: May 25, 2004

(54) DETERMINATION OF BIOLOGICALLY ACTIVE FORMS OF PROTEOLYTIC ENZYMES

(75) Inventors: Hendrik C. Hemker, Maastricht (NL); Robert J. Wagenvoord, Maastricht (NL); Manoj Ramjee, Cambridge (GB)

(73) Assignee: Synapse B.V., Maastricht (NL)

( * ) Notice: Subject to any disclaimer, the term of this patent is extended or adjusted under 35 U.S.C. 154(b) by 0 days.

(21) Appl. No.: 09/914,934

(22) PCT Filed: Mar. 3, 2000

(86) PCT No.: PCT/EP00/01912
§ 371 (c)(1),
(2), (4) Date: Nov. 21, 2001

(87) PCT Pub. No.: WO00/52199
PCT Pub. Date: Sep. 8, 2000

Related U.S. Application Data
(60) Provisional application No. 60/157,240, filed on Oct. 1, 1999.

(30) Foreign Application Priority Data
Mar. 4, 1999 (EP) .............................................. 99200627

(51) Int. Cl.$^7$ ................................................ C12Q 1/56
(52) U.S. Cl. ............................. 435/13; 435/18; 435/23; 435/24
(58) Field of Search ............................. 435/13, 18, 23, 435/24

(56) References Cited

U.S. PATENT DOCUMENTS

| | | | |
|---|---|---|---|
| 3,985,620 A | 10/1976 | Karges | 195/103.5 R |
| 4,897,444 A | 1/1990 | Brynes et al. | 525/54.1 |
| 5,073,487 A | 12/1991 | Lloyd | 435/23 |
| 5,192,689 A | 3/1993 | Hemker et al. | 436/69 |

FOREIGN PATENT DOCUMENTS

| WO | WO 96/21740 | 7/1996 |
|---|---|---|

OTHER PUBLICATIONS

Hemker et al., A Computer Asisted Method to Obtain the Prothrombin Activation Velocity in Whole Plasma Independent of Thrombin Decay Processes, Thrombosis and Haemostasis, vol. 56, No. 1, pp. 9–17 (1986) XP000567420.

Hemker et al., Continuous registration of Thrombin Generation in Plasma, Its Use for the Determination of the Thrombin Potential, Thrombosis and Haemostasis, vol. 70, No. 4, pp. 617–624 (1993) XP000567560.

Travis et al., Human Plasma Proteinase Inhibitors, Annual Review of Biochemistry, vol. 52, pp. 655–709 (1983) XP002110610.

Baret, Alpha–2–Macroglobulin, Methods in Enzymology, vol. 80, pp. 737–754 (1981) XP002110611.

*Primary Examiner*—Nashaat T. Nashed
(74) *Attorney, Agent, or Firm*—Kalow & Springut LLP

(57) ABSTRACT

A process is provided for the assessment of an active proteolytic enzyme in a blood or another biological fluid sample possibly comprising a complex of said proteolytic enzyme and $\alpha_2$-macroglobulin, wherein said sample is contacted with a substrate comprising a molecule of sufficient size coupled to a signal-substrate, said signal-substrate comprising a detectable leaving group, wherein said substrate is hydrolysed by said proteolytic enzyme but not by said complex. The proteolytic enzyme is preferably selected from the group consisting of thrombin, activated clotting factor, activated fibrinolytic factor, and activated component of the complement system. Of these, thrombin is most preferred. The molecules of sufficient size are preferably water soluble and selected from the group consisting of inert protein, preferably ovalbumin, polysaccharide, and synthetic polymer. The size of these molecules is such that they will not fit into the cavity of the $\alpha_2$M molecules.

10 Claims, 4 Drawing Sheets

DETERMINATION OF BIOLOGICALLY ACTIVE FORMS OF PROTEOLYTIC ENZYMES

This application claims the benefit of the filing date of International Application PCT/EP00/01912, filed Mar. 3, 2000 and published under International Publication Number WO 00/52199 on Sep. 8, 2000 under PCT 21(2) in English which claims the benefit of U.S. Provisional Application No. 60/157,240, filed Oct. 1, 1999. This application also claims the benefit of the filing date of U.S. Provisional Application No. 60/157,240, filed Oct. 1,1999.

FIELD OF THE INVENTION

The present invention is in the field of diagnostics and relates more in particular to a method for the determination of biologically active forms of proteolytic enzymes, such as thrombin, in blood and other fluids.

BACKGROUND OF THE INVENTION

In the Western world, arterial and venous thrombosis and atherosclerosis together are currently responsible for well over 50% of all mortality and serious morbidity. In a few decades this will be the case world-wide [Murray, C. J. and A. D. Lopez, Science (1996) 274:740–743]. Thrombosis is caused by an overactivity of the haemostatic mechanism that is responsible for the arrest of bleeding from a wound. This haemostatic-thrombotic system (HTS) is a complex interaction between vessel wall, blood cells, especially blood platelets, and plasma proteins. See, e.g., Hemker H. C. Thrombin generation, an essential step in haemostasis and thrombosis. In: Haemostasis and thrombosis, A. L. Bloom et al., eds., Churchill Livingstone, Edinburgh, (1994) 477–490.

In blood there are at least three series of proenzyme-enzyme cascades of great biological importance: the blood coagulation system, the fibrinolytic system and the complement system. In each of these systems proteolytic proenzymes are activated and subsequently inhibited. In general it is important that the concentration of an activated enzyme in such a cascade can be measured in order to assess the function of the system. In the following a typical description of the clotting system will be given with an emphasis on its most important enzyme, thrombin. It is to be noted, however, that the present invention also relates to other clotting enzymes and enzymes of the fibrinolytic and complement pathway.

The mechanism of thrombin generation can be outlined in some detail as follows. In the plasmatic coagulation system factor Xa is formed by the action of the tissue factor-factor VIIa complex (TF-VIIe). Factor Xa binds to tissue factor pathway inhibitor (TFPI) and the TFPI-Xa complex inhibits the TF-VIIa complex. Thrombin activates factors V, VIII and XI and so accelerates its own generation, but it also binds to thrombomodulin and so starts the protein C mechanism that breaks down factors V and VIII, thus, indirectly, inhibiting further thrombin generation. An important fraction (≈30%) of all thrombin formed in clotting plasma is bound to the fibrin clot. Clot-bound thrombin does retain its thrombotic properties, it can clot fibrinogen, activate factors V, VIII and XI as well as platelets [Béguin, S. and R. Kumar, Thromb. Haemost. (1997) 78:590–594; Kumar, R., S. Béguin, and H. C. Hernker, Thromb. Haemost. (1994) 72:713–721, and (1995) 74:962–968]. It is not inhibited by antithrombin.

Thrombin action causes receptors in the platelet membrane to bind fibrinogen, which causes platelet aggregation. Platelet activation also leads to the exposure of procoagulant phospholipids in a Von Willebrand factor dependent ii reaction [Béguin S., R. Kumar, I. Keularts, U. Seligsohn, B. C. Coller and H. C. Hemker, Fibrin-Dependent Platelet Procoagulant Activity Requires GPlb Receptors and Von Willebrand Factor, Blood (1999) 93:564–570; Béguin, S. and R. Kumar, supra (1997)]. These phospholipids are required for the proper activation of factor X and prothrombin. Recently, the picture has been complicated by the discovery that fibrin, previously thought to be the inert endproduct of coagulation, plays an active role itself. It binds and activates Von Willebrand factor, which activates platelets and provokes the exposure of procoagulant phospholipids via an alternative pathway.

The cooperation between platelets and the coagulation system, including fibrin, is central to the haemostatic-thrombotic system. The mechanism shows an abundance of positive and negative, often nested, feedback loops. Underactivity causes bleeding, overactivity causes thrombosis. Thrombosis manifests itself as coronary infarction, stroke, pulmonary embolism and a large number of less frequent diseases.

In order to assess the function of such a system, also for diagnostic purposes and for the safe use of antithrombotic drugs, a probe is needed for the functional status of the haemostatic-thrombotic system. An important function test of the HTS is the thrombin generation curve (TGC). Carried out in platelet-poor plasma, it gives information about the function of the plasmatic clotting system. In platelet-rich plasma it measures also the function of the platelets.

According to the prior art the TGC can be measured by subsampling or continuously. In the ancient subsampling method [Biggs, R. and R. G. Macfarlane, *Human Blood Coagulation and its Disorders*. 1953, Oxford: Blackwell; Quick, A. J., *Haemonhagic Diseases*. 1957, Philadelphia: Lea & Febiger], samples are taken from a clotting mixture, and the concentration of thrombin is measured in each sample.

Active thrombin survives in plasma for only a limited period of time (the half life time is 16–17 s). This is due to circulating antithrombins. Most thrombin (64%) is inactivated by antithrombin (AT), a plasma-protein of 57 kD, 23% by $\alpha_2$-macroglobulin ($\alpha_2$M), a 725 kD plasma-protein, and 13% by various other agents [Hemker, H. C., G. M. Willems, and S. Béguin, A computer assisted method to obtain the prothrombin activation velocity in whole plasma independent of thrombin decay processes, Thromb. Haemost. (1986) 56:9–17]. The $\alpha_2$-macroglobulin-thrombin complex ($\alpha_2$M-IIa) has the peculiarity that it is inactive towards all macromolecular substrates, but retains its activity against small molecular weight (artificial) substrates. $\alpha_2$-Macroglobulin is a glycoprotein of Mr 725,000, which is present in plasma in a concentration of 2500 mg/L or 3.5 $\mu$M. It is a tetramer of identical subunits of 185 kD. The inactivation reaction of an active proteinase or activated clotting factor with $\alpha_2$M is a three step process: 1°. Formation of a loose complex, 2°. Hydrolysis of a target peptide in $\alpha_2$M, causing 3°, a rapid conformational change which physically entraps the enzyme molecule within the $\alpha_2$M molecule. [See for a review: Travis, J. and G. S. Salvesen, Human plasma proteinase inhibitors. Ann. Rev. Biochem. (1983) 52:655–709].

The group of Hemker then developed a continuous method in which thrombin-catalysed product formation from suitable substrates is monitored directly [Hemker, H. C., et al., Continuous registration of thrombin generation in plasma, its use for the determination of the thrombin potential. Thromb. Haemost. (1993) 70:617–624]. The kinetic constants of the substrate are such that, at the concentration used, the rate of product formation is proportional to the amount of enzyme present (thrombin or $\alpha_2$M-IIa). The time-course of enzyme activity in the sample can be estimated as the first derivative of the product-time curve.

A drawback of this method is that part of the thrombin in plasma binds to $\alpha_2$-macroglobulin. $\alpha_2$-Macroglobulin is the most abundant non-specific protease inhibitor of blood plasma. It quenches the biological activity of proteases (activated clotting factors, activated fibrinolytic enzymes and activated complement factors) without occupying their active centre, so that there is a residual activity on the usual oligopeptide signal-substrates.

This $\alpha_2$-macroglobulin-thrombin complex has no known physiological activity but is able to cleave chromogenic substrates. Thus, the product formation observed is the result of the combined activities of free thrombin and $\alpha_2$-macroglobulin-bound thrombin. The relevant data, i.e., the amount of product formed by free thrombin only, can be extracted from the experimental product formation by a mathematical operation. However, the operation has to be carried out on the whole course of the product generation curve. The product formation therefore needs to be monitored continuously. Although the principle of this continuous method is applicable to all substrates that give a product which can be detected in time, e.g., by fluorescent, electrochemical or NMR signals, its application is currently restricted to the use of chromogenic substrates in an optically clear medium, i.e., defibrinated platelet poor plasma (PPP).

Therefore, there is still a need for an efficient method to measure the amount of (active forms of proteolytic enzymes, such as thrombin, in blood and other fluids, which obviates the drawbacks of the prior art. The present invention provides such a method.

SUMMARY OF THE INVENTION

In accordance with the present invention, a process is provided for the assessment of an active proteolytic enzyme in a blood or another biological fluid sample possibly comprising a complex of said proteolytic enzyme and $\alpha_2$-macro-globulin, wherein said sample is contacted with a substrate comprising a molecule of sufficient size coupled to a signal-substrate, said signal-substrate comprising a detectable leaving group, wherein said substrate is hydrolysed by said proteolytic enzyme but not by said complex.

The active proteolytic enzyme is preferably selected from the group consisting of thrombin, activated clotting factor, activated fibrinolytic factor, and activated component of the complement system. Of these, thrombin is most preferred.

The molecules of sufficient size are preferably selected from the group consisting of inert protein, preferably ovalbumin, polysaccharide, and synthetic polymer. Preferably, these inert molecules are water soluble and have a size such that they just do not fit into the cavity of the $\alpha_2$M molecules. A group of preferred inert molecules has a size of about 40 kD and a solubility of at least 40 mg/ml. Most preferred are inert molecules with a size of about 20 kD and a solubility of at least 50 mg/ml.

These and other aspects of the invention will be further outlined in the description which follows.

DETAILED DESCRIPTION OF THE INVENTION

Figure 1:
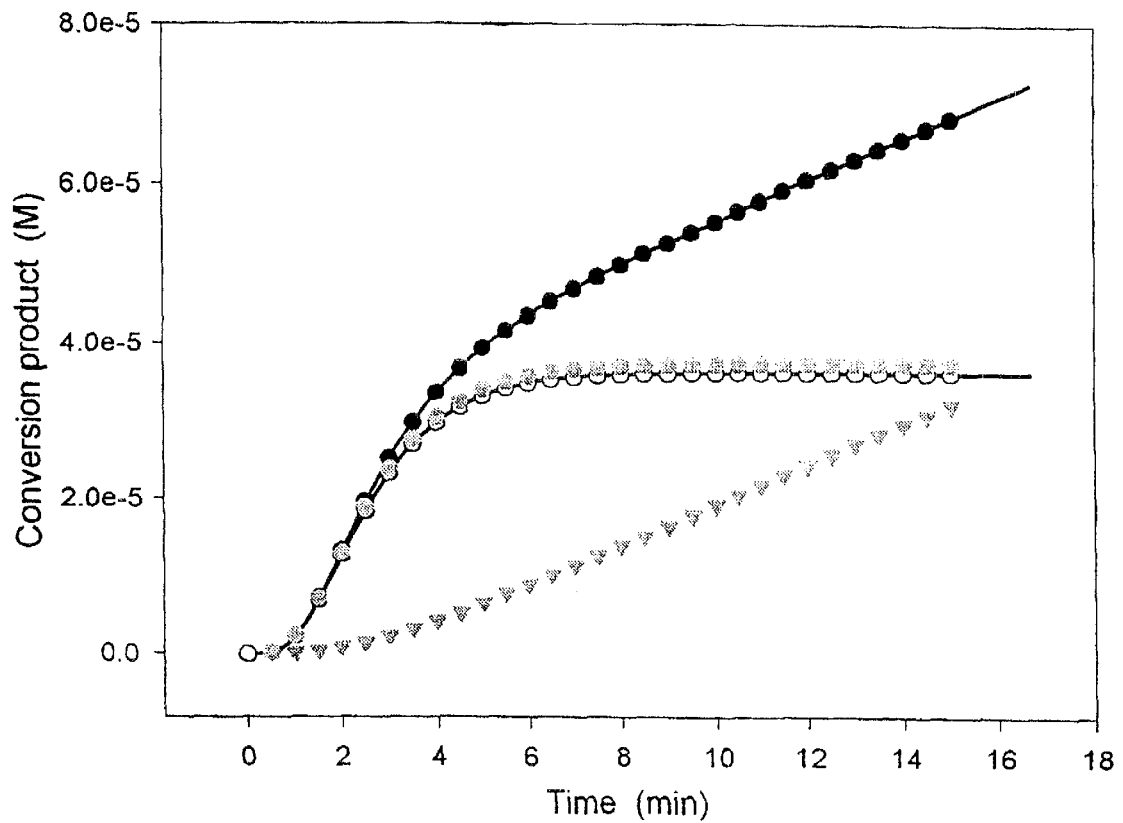
FIG. 1 represents theoretical curves of hydrolysis products formed in clotting plasma or bloody by hydrolysis of a small thrombin substrate and a large thrombin substrate. Closed black circles indicate the total hydrolysis of a small thrombin substrate; closed gray circles indicate hydrolysis by temporarily present thrombin of a small thrombin substrate; open circles indicate hydrolysis of a large thrombin substrate; closed triangles indicate hydrolysis by formed $\alpha_2$-macroglobulin-thrombin complex of a small thrombin substrate.

The present invention is based on the surprising finding that certain signal-substrates for proteolytic enzymes, notably thrombin substrates, are cleft by thrombin but not by the $\alpha_2$-macroglobulin-thrombin complex. Thus, these signal-substrates are insensitive to the action of proteolytic enzymes when they are bound to $\alpha_2$-macroglobulin.

As used herein, the term "signal-substrate" means a substrate that is cleaved by proteolytic enzyme(s) present in the medium, from which a leaving group is split off which is detectable by optical, NMR or other methods. Leaving groups which are optical detectable are, for example, p-nitroanilide and 7-amido-4-methyl-coumarin. p-Nitroanilide absorbs at 405 nm and 7-amido-4-methyl-coumarin is fluorescent (excitation at 390 nm and emission at 460 nm). Examples of NMR-active leaving groups are those containing $^{31}$p, $^{13}$C, or any other atom which can be detected with NMR or a similar technique. Also H$^+$ ions can be used as leaving group, which can be detected by measuring changes in the pH.

The present invention has the advantage that the total transient enzymatic activity of the free thrombin in the clotting sample can be assessed from the total amount of substrate that is converted, so that the mathematical procedure can be omitted.

The formation of thrombin in clotting blood or plasma arises from prothrombin by an enzymatic controlled reaction, which is called prothrombinase. Initially this reaction is slow, but the rate increases exponentially until the formed thrombin activates the inactivators of the prothrombinase and the prothrombin is exhausted.

We have found that the formation of thrombin can be fitted into the following mathematical equation:

$$FIIa_t = PT \cdot (1 - e^{-b \cdot t}) c \quad \text{(i)}$$

in which $FIIa_t$ is the formation of thrombin in time, PT is the initial amount of prothrombin, b and c are constants and t is the time. By fitting an actually measured thrombin generation curve with this formula one finds a very good agreement between the fit and the data when b=0.02 and c=4.

The formed thrombin will react with the plasmatic inhibitors, from which AT and $\alpha_2 M$ are the most important. The reaction constants (decay constants) of these reaction are about 20,000 $(M.s)^{-1}$ and 1,500 $(M.s)^{-1}$, respectively.

If the amount of thrombin is to be measured continuously, a thrombin substrate is added to the reaction mixture. By the action of thrombin a molecule is split off from the substrate which can be measured, for example in a spectrophotometer or a fluorometer.

It has now been found, after extensive research and experimentation, that in contrast to small substrates, when using a relatively bulky thrombin substrate, hydrolysis stops when all thrombin has been inactivated, and the total enzymatic activity of thrombin can be measured as an end-point assay.

Accordingly, in one aspect of the present invention there are provided large size chromogenic and fluorogenic and other signal-substrates, to the extent that they cannot penetrate into the cavity of the $\alpha_2 M$ molecule and thus are not hydrolysed by $\alpha_2 M$-IIa. This is achieved by coupling the signal-substrate to an inert bulky carrier molecule which results into a "substrate". The coupling is preferably carried out chemically, in a way which is known to a man skilled in the art.

The exclusion limit of the cavity of $\alpha_2 M$ in which an active protease is entrapped is about 10 kD (Barrett, A., *Methods in Enzymol.* (1981) 80:737–754]. Thus, suitable inert carrier molecules are larger than 10 kD and include, for example, proteins, polysaccharides, synthetic polymers. Preferably, the inert molecules have a good solubility. One preferred group of inert molecules has a size such that the molecules just do not fit into the cavity of the $\alpha_2 M$ molecule. Another group of preferred inert molecules has a size of about 40 kD and a solubility of at least 40 mg/ml. Most preferred are inert molecules with a size of about 20 kD and a solubility of at least 50 mg/ml.

Suitable and preferred proteins are those which are commercially available, such as ovalbumin (Mr=45 kD), bovine serum albumin (Mr=67 kD), human serum albumin (Mr 67 kD) and hen-egg white lysozyme (Mr=14.4 kD).

Suitable polysaccharides have a Mr which may vary from a few kD (so that they do not fit into the $\alpha_2 M$ cavity) to more than 500 kD. An example of such a polysaccharide is dextran.

Suitable synthetic polymers include hydrophilic water soluble polymers, with a Mr also varying from a few kD to more than 500 kD, such as polyacrylic acid, polyethylene oxide, polyvinyl chloride, poly(1-vinylpyrrolidone-co-acrylic acid), poly(2-hydroxyethyl methacrylate), and the like.

Suitable signal-substrates for the purpose of the present invention are compounds with a leaving group which can be easily detected and which is not split by the $\alpha_2$-macroglobulin-protease complex. The leaving group preferably gives an optical density signal or a fluorescent signal. Examples of such leaving groups include p-nitroanilide and 7-amino-4-coumarin, respectively.

Suitable substrates for the purpose of the present invention include compounds which are obtained by coupling a signal-substrate of relatively low Mr to a inert molecule of sufficient size. Examples of suitable substrates include ovalbumin coupled to H-D-isoleucyl-L-prolyl-L-arginine-p-nitroanilide.2HCl (also referred to as "OA-S2288"), ovalbumin coupled to H-alanyl-L-arginine-7-amido-4-methylcoumarin (also referred to as "OA-Ala-Arg-AMC"), and ovalbumin coupled to H-D-phenylalanyl-L-prolyl-L-lysine-p-nitroanilide.2HCl (also referred to as "OA-Phe-Pro-Lys-pNA"). Another example of a suitable substrate is ovalbumin coupled to a signal-substrate releasing one or more hydrogen ions as leaving group.

When such a substrate is used to measure the thrombin generation curve (TGC), the temporary thrombin will hydrolyse a certain amount of substrate, after which no further hydrolysis will take place. The amount of the substrate, as well as the kinetic properties thereof, are preferably so chosen that the amount of thrombin generated in the plasma (or other medium) does not consume the substrate completely. The end-level of conversion product formed can be measured and is directly proportional to the surface under the TGC, which is called the endogenous thrombin potential (ETP).

The substrates can be suitably used to measure the biologically active form of proteolytic enzymes in blood and other fluids containing $\alpha_2$-macroglobulin. An important application is the generation and disappearance of thrombin in clotting blood, which is an important function test of the haemostatic-thrombotic system (HTS).

Although the present invention is typically described and exemplified for the assessment of (generated) thrombin in blood and other biological fluids, it will be understood that the method is also suitable for the assessment of other proteolytic enzymes in such biological fluids using possible variations and modifications which are clear to the man skilled in the art. Examples of such other proteolytic enzymes include activated clotting factor, activated fibrinolytic factor, and activated component of the complement system.

The invention is further illustrated by the following Examples which should not be construed as limiting the invention in any respect.

EXAMPLE 1

Hydrolysis of a Thrombin Substrate in Clotting Blood or Plasma

To blood or plasma 0.5 mM thrombin substrate is added and blood coagulation starts by calcification and a suitable trigger, in this example typically thromboplastin. FIG. 1 shows the theoretical curves of the formation of conversion products in time.

The curves (-●- or -○-) show the hydrolysis of a thrombin substrate in clotting plasma. We assume that thrombin formation occurs to equation (i), see the Detailed Description, with the constants mentioned therein. The formed thrombin will react with both AT and $\alpha_2 M$. The AT concentration is set to 2.5 $\mu M$ and the $\alpha_2 M$ concentration to 3.5 $\mu M$. The reaction constant of thrombin inactivation by AT is 20,000 $(M.s)^{-1}$, and that of thrombin inactivation by $\alpha_2 M$ is 1,450 $(M.s)^{-1}$. To design the curves numerical methods have been used. We used steps of 1 s. After 1 s an amount of thrombin is formed as indicated by equation (i). From 1 to 2 seconds this amount of thrombin will react with AT and $\alpha_2 M$ at a rate determined by the above given constants. After this second some AT-thrombin complex (AT-IIa) and $\alpha_2 M$-IIa is formed. These amounts are subtracted from the present amount of thrombin, but new thrombin is formed in this second according to equation (i). From 2 to 3 seconds the new amount of thrombin will react with AT and $\alpha_2$M (both corrected for the complexes) while new AT-IIa and $\alpha_2$M-IIa is formed and thus some thrombin is inactivated. This process is repeated during the time span of 15 min. Thus, we see the build up of AT-IIa and $\alpha_2$M-IIa during the process and a temporary increase of thrombin, followed by complete inactivation of thrombin by AT and $\alpha_2$M.

By addition of a small thrombin substrate to this mixture two new reactions are introduced: S is hydrolysed by free thrombin and by $\alpha_2$M-IIa. When S is a large substrate, it will be hydrolysed by the free thrombin, but not by $\alpha_2$M-IIa. These reactions will follow Michaelis-Menten kinetics: hydrolysis rate=[Thrombin].$k_{cat}$.S/($K_m$+S).

The amount of hydrolysis product is calculated with the numerical procedure described above. In case of curve -●-, S is a small thrombin substrate and in case of curve -○- S is a large thrombin substrate.

The thrombin substrate (S) is hydrolysed by thrombin with a $K_m$ of 500 μM and a $k_{cat}$ of 1 s$^{-1}$. Also $\alpha_2$M-IIa hydrolyses S, in case of curve -●-$K_m$ is 500 μM and $k_{cat}$ is 0.5 s$^{-1}$ and in case of curve -○-$K_m$ is 1 M and $k_{cat}$ is zero (i.e. S is not hydrolysed).

In this Example a model substrate is used with the kinetics given above. In actual practice substrates are available with kinetics which are close to this model. Suitable and preferred examples of such substrates are SQ68, Msc-Val-Arg-pNA, DEMZ-Gly-Arg-pNA, and Petachrome TH/SR.

The above procedure is usually applied in a somewhat modified form in that the process is not monitored continuously but samples are taken every 30 sec and the formed conversion product (indicated by the circles ● or ○) measured.

When using a small thrombin substrate, which procedure was routinely used prior to the present invention, curves were obtained as shown by -+-. In order to determine the amount of conversion product formed by the action of free thrombin, the curve was split into two parts, product formation by free thrombin and $\alpha_2$M-IIa, respectively. Product formation by free thrombin will stop when all thrombin has been inactivated, but product formation by $\alpha_2$M-IIa will continue. This explains the ongoing linear product formation at the end of curve -●-. The collection of data measured had to be split into one set for product formation by free thrombin and one set for product formation by $\alpha_2$M-IIa. For this procedure a mathematical algorithm has been developed [Hemker, H. C., S. Wielders, H. Kessels and S. Béguin, Continuous registration of thrombin generation in plasma, its use for the determination of the thrombin potential. Thromb. Haemost. (1973) 70:617–624]. The principle is the following. At t=0 no thrombin and no $\alpha_2$M-IIa is present and the signal is set to zero. At t=0.5 min (second measured data point) an increased signal is measured due to S hydrolysis by thrombin and $\alpha_2$M-IIa. A fraction of this signal (k×$\alpha_2$M-IIa concentration) is due to $\alpha_2$M-IIa. At t=1 min, the signal is increased due to S hydrolysis by free thrombin by the present amount of $\alpha_2$M-IIa. This procedure is continued until the last data point is reached. From the theoretically derived curve an the actual observations we know that at the end of the curve all free thrombin has been inactivated and the increase of the signal is completely due to S hydrolysis by $\alpha_2$M-IIa. By choosing the k at which the last part of the curve becomes minimal (i.e. the formation of product is constant in time) the data set can be split into a signal due to S hydrolysis by free thrombin (-○-) and a signal due to the effect of $\alpha_2$M-IIa (-▽-).

It is noted that the signal caused by the free thrombin reaches a plateau which remains the same, independent on the method used. When a small thrombin substrate is applied, this ceiling has to be determined with a mathematical algorithm. However, when a large thrombin substrate is used according to the present invention, the plateau can be easily determined by reading the end-level of signal.

EXAMPLE 2

Hydrolysis of Ovalbumin Substrate OA-S2288 by $\alpha_2$M-IIa and Thrombin

In this example it is shown that by coupling of ovalbumin to S2288 the substrate loses its ability to be hydrolysed by $\alpha_2$M-IIa, but not by thrombin. This substrate (OA-S2288) was prepared in the following way. A reaction mixture was prepared containing 1 mM S2288, 50 mM sodium carbonate (pH 10.2), 20 mg/ml ovalbumin and 3.6 mg/ml bis (sulfosuccinimidyl)suberate (BS$^3$) This mixture was incubated for 30 min at room temperature, then 50 mM Tris (pH 8.2) was added and the mixture was kept at room temperature for 30 min. The mixture was applied to a Sephadex G25 column (16×1.6 cm$^3$) and eluted with a rate of 3 ml/min. The elution buffer was 50 mM HEPES, 100 mM NaCl (pH 7.35). The first peak that eluted from the column contained the ovalbumin coupled to the S2288 (OA-S2288).

The amidolytic activity of human thrombin and human $\alpha_2$M-IIa towards OA-S2288 was measured. The reaction mixtures contained 22 μM OA-S2288, 50 nM thrombin or $\alpha_2$M-IIa and 175 mM NaCl, 50 mM Tris-HCl, 2 mg/ml ovalbumin (pH 7.9).

Figure 2:
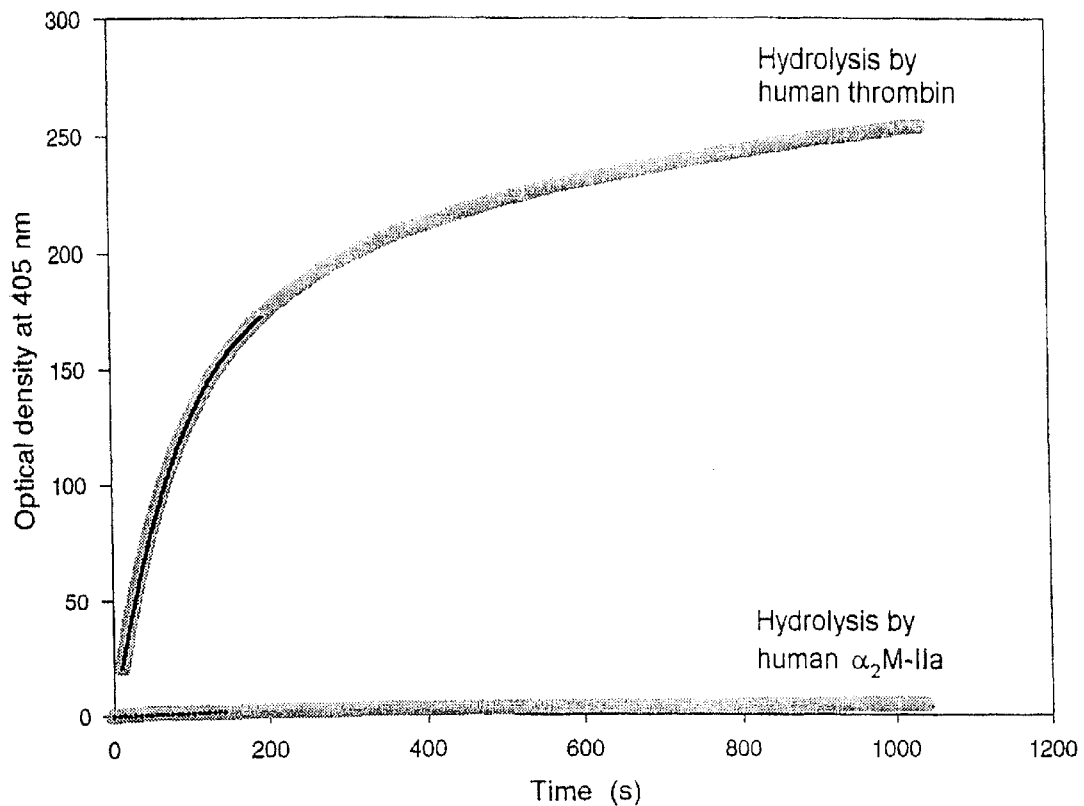
FIG. 2 represents the curves of hydrolysis products of substrates S2288 coupled with ovalbumin by hydrolysis with $\alpha_2$M-IIa and thrombin, respectively. For each curve, the thick gray overlaid curve represents actually measured curves, whereas the thin black curve beneath the thick gray overlaid curve represents the obtained fits.

In FIG. 2 the amount of free p-nitroanilide (pNA) formed, expressed as milli optical density at 405 nm, is plotted against the time. The reaction temperature was 37° C. The grey curves are the measured data, whereas the black line is obtained by fitting, assuming that product formation occurs according to Michaelis-Menten kinetics.

Product formation in time can be described as: E.$k_{cat}$. $S_t$/($K_m$+$S_t$), in which $S_t$ is the substrate concentration in time (i.e. the substrate concentration originally present ($S_0$) minus the formed product or split substrate, and E is the enzyme that splits the substrate, either thrombin or $\alpha_2$M-IIa.

The following constants were found: $S_0$=22 μM, $K_m$=1.47 μM and $k_{cat}$=0.31 s$^{-1}$ for E is thrombin and 0.002 s$^{-1}$ for E is $\alpha_2$M-IIa.

EXAMPLE 3

Figure 3:
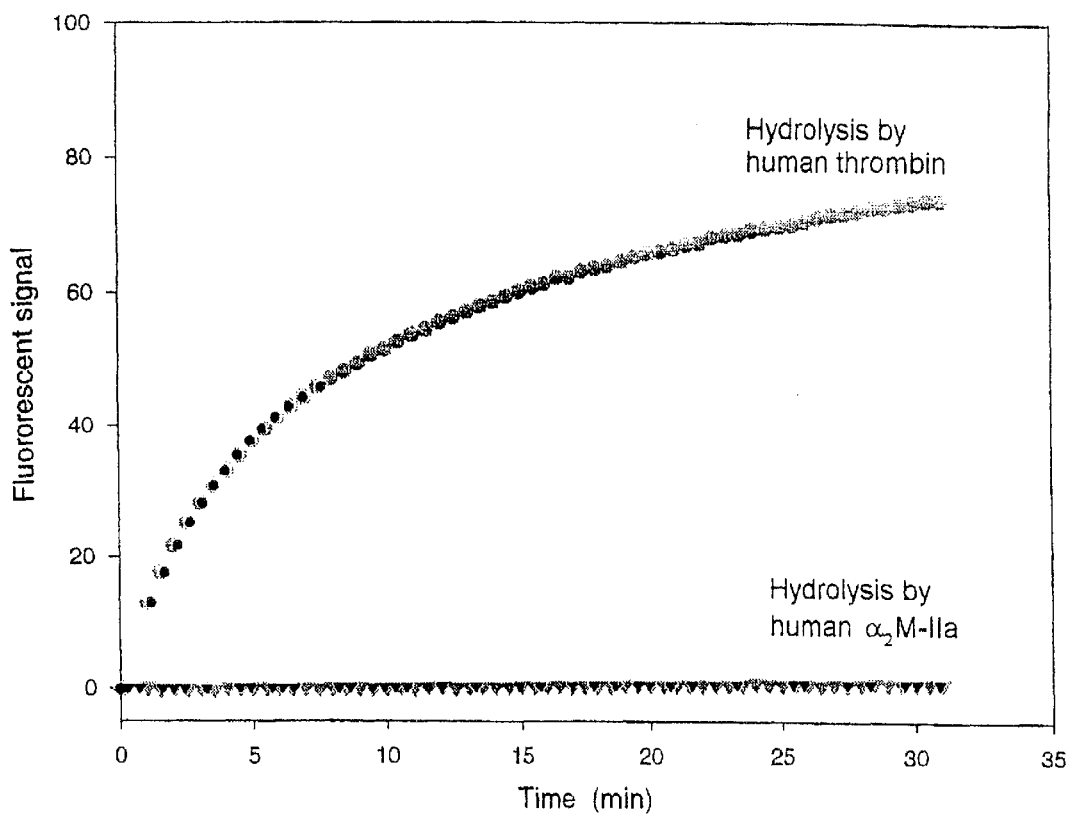
FIG. 3 represents the fluorescence patterns of the fluorescent substrate Ala-Arg-AMC coupled with ovalbumin by hydrolysis with free thrombin and thrombin inactivated by $\alpha_2$M, respectively. The upper curve represents hydrolysis by human thrombin, in which the open circles are actually measured points; the closed black circles are obtained by fitting. The lower curve represents hydrolysis by human $\alpha_2$-macroglobulin-thrombin complex, in which the open triangles are actually measured points; the closed triangles are obtained by fitting.

Hydrolysis of Ovalbumin Substrate OA-Ala-Arg-AMC by Free Thrombin and Thrombin Inactivated by $\alpha_2$M This example shows that by coupling of ovalbumin to the fluorescent substrate Ala-Arg-AMC, the substrate will not be split anymore by thrombin entrapped in the cavity of $\alpha_2$M. FIG. 3 shows that free thrombin splits off the fluorescent group (AMC), but that thrombin inactivated by $\alpha$2M cannot.

The coupling of ovalbumin to Ala-Arg-AMC was carried out as follows. To 1 ml of a 1 mg/ml ovalbumin in PBS=10 mM potassium phosphate, 150 mM NaCl, pH 7.4) was added 6 μl of 50 mM BS$^3$ in 100% dimethylsulfoxide. The mixture was incubated at room temperature for 60 min. and dialysed twice against 2 L PBS (each for 2 h). Then 5 μl of 100 mM Ala-Arg-AMC was added and incubated at room temperature for 60 min. Finally, the sample was dialysed as before (twice against 2 L PBS).

FIG. 3 shows the results of fluorescence measurements in a Fluoroskan Acsent equipped with a thermostated block, a 390 nm excitation and 460 nm emission filter. The assay was carried out at 25° C. in 96 well Microfluor W "U" bottomed micro titre plates (Dynex, London, UK) in 10 mM HEPES, 5 mM $CaCl_2$, 0.02% sodium azide, pH 8.0). In case of -○- the vessel contained 5.5 µM OA-AR-AMC (Ala-Arg-AMC coupled to ovalbumin) and 85 nM human thrombin and in case of -▽-5.5 µM OA-AR-AMC and 65 µM human α2M-IIa. The black symbols (-●- and -▼-) were obtained by fitting assuming that the substrate is hydrolysed by thrombin according to Michaelis-Menten kinetics. From the fitting the following constants were found for hydrolysis by thrombin: the substrate concentration $S_0$=5.5 µM, $K_m$=1.2 µM and $k_{cat}$=3.3 $s^{-1}$. For hydrolysis by $α_2$M-IIa the already derived $S_0$ and $K_m$ were found and $k_{cat}$=0.008 $s^{-1}$.

EXAMPLE 4

Determination of the ETP in Plasma With SQ68 and OA-Phe-Pip-Lys-pNA

Figure 4:
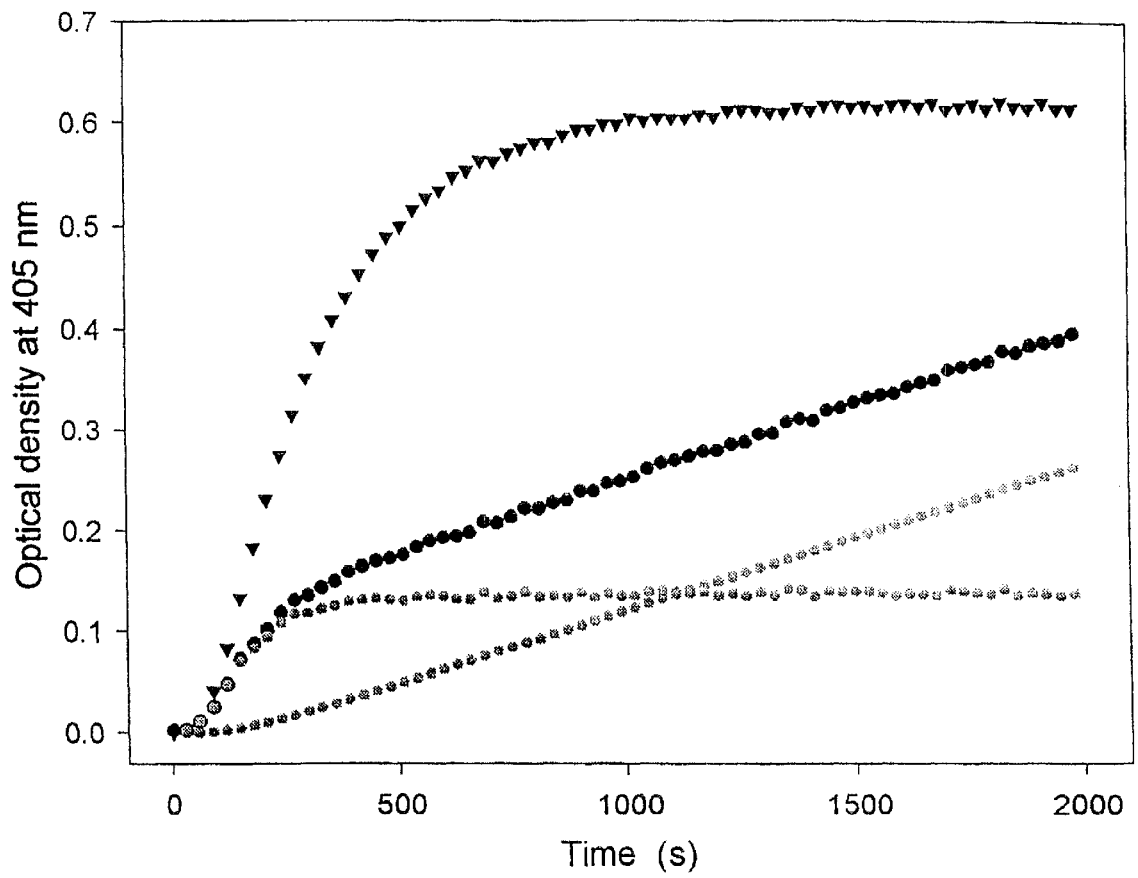
FIG. 4 shows the results of the determination of the ETP in plasma with SQ68 and OA-Phe-Pip-Lys-pNA. Closed triangles represent hydrolysis of OA-Phe-Pip-Lys-pNA in clotting plasma; closed circles represent hydrolysis of SQ68 in clotting plasma; open circles represent hydrolysis of SQ68 in clotting plasma by formed $\alpha_2$-macroglobulin-thrombin complex; open triangles represent hydrolysis of SO68 in clotting plasma by temporarily present thrombin.

See FIG. 4. Thrombin generation was measured as described earlier [Hemker, H. C., Wielders, S., Kessels, H., Béguin, S. Continuous Registration of Thrombin Generation in Plasma, its Use for the Determination of the Thrombin Potential. Thromb. Haemost. (1993) 70:617–624, and Hemker, H. C. and Béguin S. Thrombin generation in plasma: its assessment via the endogenous thrombin potential. Thromb. Haemost. (1995) 74:134–138].

Formation of pNA in clotting plasma to which was added SQ68 (●) or OA-Phe-Pip-Lys-pNA (▼); Pip is pipecolyl. The pNA formation was monitored by measuring the optical density at 405 nm. The substrate concentration was 0.5 mM in both cases. The data set obtained with SQ68 was analysed and split into pNA formed by free thrombin (⊕) and pNA formed by $α_2$M-IIa (▽), using the algorithm described in Example 1.

It can be clearly seen that when using a substrate according to the present invention, experimental data are obtained in a very efficient way which represent directly the same biological activity (i.e. the amount of substrate split by free thrombin) as those which are obtained from a complex mathematical dissection of the curve from a conventional substrate.

It is to be understood that modifications and changes to the preferred embodiment of the invention can be made without departing from the spirit and scope of the present invention.

What is claimed is:

1. A process for the assessment of an active proteolytic enzyme in blood or another biological fluid sample comprising contacting said sample with a water soluble substrate comprising a molecule having a molecular weight larger than 10 kD coupled to a signal-substrate, said signal-substrate comprising a detectable leaving group, wherein said substrate is hydrolyzed by said proteolytic enzyme but not by a complex of said proteolytic enzyme and $α_2$-macroglobulin.

2. The process of claim 1, wherein the active proteolytic enzyme is thrombin.

3. The process of claim 1, wherein the molecule having a molecular weight larger than 10 kD is a water soluble inert protein, a polysaccharide, or a synthetic polymer.

4. The process of claim 3, wherein the inert protein is ovalbumin.

5. The process of claim 1, wherein the molecule having a molecular weight larger than 10 kD has a molecular weight of about 40 kD and a solubility of at least 40 mg/ml.

6. The process of claim 1, wherein the molecule having a molecular weight larger than 10 kD has a molecular weight of about 20 kD and a solubility of at least 50 mg/ml.

7. The process of claim 1, wherein the leaving group gives an optical density signal or a fluorescent signal.

8. The process of claim 7, wherein the leaving group is p-nitroanilide or 7-amino-4-methyl-coumarin.

9. The process of claim 1, wherein the substrate is selected from the group consisting of ovalbumin coupled to H-D-isoleucyl-L-prolyl-L-arginine-p-nitroanilide.2HCl, ovalbumin coupled to H-alanyl-L-arginine-7-amido-4-methyl-coumarin, and ovalbumin coupled to H-D-phenylaianyl-L-prolyl-L-lysine-p-nitroanilide.2HCl.

10. The process of claim 1, wherein the substrate is not fully consumed during the course of measurement.

* * * * *